United States Patent [19]
Lawrence

[11] Patent Number: 6,031,335
[45] Date of Patent: Feb. 29, 2000

[54] ELECTRICAL POWER CONTROL SYSTEM FOR LIGHTING SYSTEMS

[76] Inventor: John Arthur Lawrence, Laburnham House, Nutley, East Sussex, TN 22 3LX, United Kingdom

[21] Appl. No.: 08/820,191

[22] Filed: Jan. 17, 1997

[30] Foreign Application Priority Data

| Jul. 20, 1994 | [GB] | United Kingdom | 9414655 |
| Mar. 3, 1995 | [GB] | United Kingdom | 9504282 |
| Jul. 20, 1995 | [EP] | European Pat. Off. . PCT/GB95/01729 | |

[51] Int. Cl.[7] .................................................. H05B 37/00
[52] U.S. Cl. ........................ 315/119; 315/123; 315/276; 307/132 R
[58] Field of Search .................................. 315/291, 297, 315/276, 277, 141, 119, 123; 307/128, 129, 130, 131, 132 R

[56] References Cited

U.S. PATENT DOCUMENTS

| 4,189,664 | 2/1980 | Hirschfeld | 315/297 |
| 4,201,938 | 5/1980 | Neumann | 323/43.5 R |
| 4,237,403 | 12/1980 | Davis | 315/98 |
| 4,513,224 | 4/1985 | Thomas | 315/141 |

FOREIGN PATENT DOCUMENTS 8803353  5/1988  WIPO .

*Primary Examiner*—David H. Vu
*Attorney, Agent, or Firm*—Laubscher & Laubscher

[57] ABSTRACT

An electrical power system to provide a selected voltage to a load such as a fluorescent lighting system is characterized by a winding 3 having a positive end connected to a positive rail and is tapped at a predetermined position for supplying an output terminal with a selected voltage. A first relay contact can electrically connect a neutral end of the winding to a neutral rail to provide one selected voltage or a second relay contact can electrically short-circuit a predetermined number of turns of the winding in response to a request for a second selected voltage. When a fault condition is monitored, a third relay contact can electrically short-circuit the neutral end of the winding to the predetermined position to put the system into a failsafe condition which prevents turns of the winding being open circuit.

17 Claims, 3 Drawing Sheets

ELECTRICAL POWER CONTROL SYSTEM FOR LIGHTING SYSTEMS

The present invention relates to an electrical power control circuit and more particularly to an electrical power control circuit for electrical lighting systems, for example fluorescent lighting systems in large commercial buildings.

BRIEF DESCRIPTION OF THE PRIOR ART

A known power control system for providing a reduced voltage to fluorescent lamps in an electrical lighting arrangement is disclosed in WO 88/03353. In this document, a transformer provides a reduced voltage which can be supplemented by a further transformer up to a normal main voltage for the purpose of enabling the fluorescent lamps to strike. The further transformer is then disabled so that the reduced voltage is again applied for running the lighting system thereby reducing power consumption. Of course any voltage reduction should not result is a perceptibly dimmer light output.

Another known power control system for providing a reduced voltage to fluorescent lamps in an electrical lighting system involves the use of a plurality of switchable transformers which at start up are switched out so that a normal main voltage is applied directly to the lighting. Then, they are switched in to provide the reduced lighting. However, there will be a power surge generated when disconnecting the transformer if it is operating. For example, a 10 KVA transformer for a bank of up to 200 lamps, could generate a surge of 400 amps when switched in this way. Among other things, the switching contacts would rapidly degrade leading to un-reliability. Thus, these type of systems have not been used due to their failure rate.

SUMMARY OF THE INVENTION

It is an object of the present invention to provide an electrical power supply circuit which overcomes the above problems with switching transformers.

According to one aspect of the present invention there is provided a method of controlling an electrical power system for providing one of a plurality of selected voltages to a load, the method comprising the steps of:
 (a) electrically connecting one end of a winding to the positive terminal of a source of electrical power, the winding being tapped at a predetermined position for supplying an output terminal with a selected voltage;
 (b) enabling a terminal connection device to electrically connect the other end of the winding to a neutral terminal of the source of electrical power in response to supply of power being required;
 (c) excluding a predetermined number of turns of the winding in response to a request for another selected voltage;
 (d) monitoring for at least one type of fault condition; and
 (e) electrically disconnecting the winding from the neutral terminal and electrically short-circuiting the other end of the winding to the predetermined position when a fault condition is monitored.

In this way, the present invention can provide a number of different output voltages at the output terminal according to demand. Furthermore, when a fault condition is monitored, a failsafe condition is provided wherein the effect of the winding is taken out of the circuit in a safe way by disconnecting the winding from the neutral terminal and preventing turns of the winding being open. Accordingly, damage to the winding and circuitry of the system in general is avoided.

Preferably, step (c) comprises disabling the terminal connection means to electrically disconnect the other end of the winding from the neutral terminal and enabling a switching device to electrically connect to the neutral terminal to exclude the predetermined number of turns of the winding located from the other end of the winding.

Thus, it is possible to short-circuit just the turns of the winding towards the other end of the winding which was connected to the neutral terminal. This is effected towards the neutral terminal end thereby enabling better performance from the connection device and switching device since smaller currents are encountered.

Conveniently, step (e) comprises disabling the terminal connection device and the switching means and enabling a further switching device to electrically short-circuit the other end of the winding to the predetermined position.

In this way, the winding can be disconnected from the neutral terminal in a safe and effective manner while preventing turns of the winding from being open.

In a preferred embodiment, the method further comprises the step of monitoring for an increased load demand and stopping step (c) in response to a predetermined load demand.

As a result, while a preferred (reduced) voltage can be supplied during stable conditions, a relatively higher voltage can be supplied when an extra load demand appears.

In another embodiment, the method further comprises the step of monitoring the voltage to the one end of the winding and stopping step (c) in response to the voltage falling below a predetermined value.

As a result, while a preferred (reduced) voltage can be supplied during stable conditions, a relatively higher voltage can be supplied to compensate for when the input voltage drops.

Conveniently, the method further comprises the step of supplying the request for another selected voltage after the lapse of a predetermined time interval following supply of power being required.

In this way, another voltage can be provided in a simple, convenient and cost effective manner.

According to another aspect of the present invention there is provided an electrical power control system for providing one of a plurality of selected voltages to a load, the electrical power control system comprising:
 a positive and neutral terminal for connection to a source of electrical power;
 an output terminal for supplying a plurality of selected voltages;
 a winding having one end electrically connected to the positive terminal and being tapped at a predetermined position for supplying the output terminal with a selected voltage;
 a terminal connection device capable of being enabled to electrically connect the other end of the winding to the neutral terminal;
 a switching device capable of being enabled to exclude a predetermined number of turns of the winding in response to a request for another selected voltage;
 monitoring means for monitoring at least one type of fault condition; and
 further switching means capable of being enabled to electrically short-circuit the other end of the winding to the predetermined position when a fault condition is monitored.

In this way, different output voltages can be provided at the output terminal according to demand, yet when a fault condition is monitored, a failsafe condition is effected wherein the effect of the winding is removed in a safe way so that damage to the winding and circuit of the system is avoided.

Preferably, the switching means is connected to the neutral terminal to exclude the predetermined number of turns of the winding from the other end of the winding.

In one case, in response to monitoring of a fault condition, the monitoring means disables the terminal connection device and the switching device to electrically disconnect the other end of the winding from the neutral terminal and enables the further switching device.

In a preferred embodiment, the monitoring device further comprises a current demand sensing device for sensing for transient current changes in the current demand by the load; wherein the monitoring device disables the switching device in response to transient changes in current above a predetermined level.

In another preferred embodiment, the monitoring device further comprises a current overload monitoring device for monitoring current to the winding; wherein the monitoring device disables the terminal connection device and the switching device to electrically disconnect the other end of the winding from the neutral terminal and enables the further switching device in response to a monitored current above a predetermined maximum level.

In still another preferred embodiment, the monitoring device further comprises a voltage monitoring device for monitoring voltage to the one end of the winding; and wherein the monitoring device disables the switching device in response to a voltage below a predetermined minimum.

Conveniently, the monitoring device further comprises a timer device for measuring the time starting from a supply of the selected voltage; wherein the monitoring device enables the switching device when the measured time exceeds a predetermined time interval.

In one case, the timer device monitors a further time starting from supply of the selected voltage; wherein the monitoring device enables the switching device only when the further time exceeds a further predetermined time interval during which the voltage to the one end of the winding has not fallen below the predetermined minimum.

By having two time intervals arranged in this way, unnecessary changes in the system are not made until stable conditions have been attained.

It is preferred that the timer device is reset whenever the switching device is disabled or the further switching device is enabled.

Conveniently, the terminal connection device, the switching device and the further switching device comprise relay contacts.

It is preferred that the system further comprises a zero crossing detector so that movement of the relay contacts can take place at zero crossing points.

BRIEF DESCRIPTION OF THE FIGURES

Examples of the present invention will now be described with reference to the accompanying drawing, in which.

DETAILED DESCRIPTION

Figure 1:
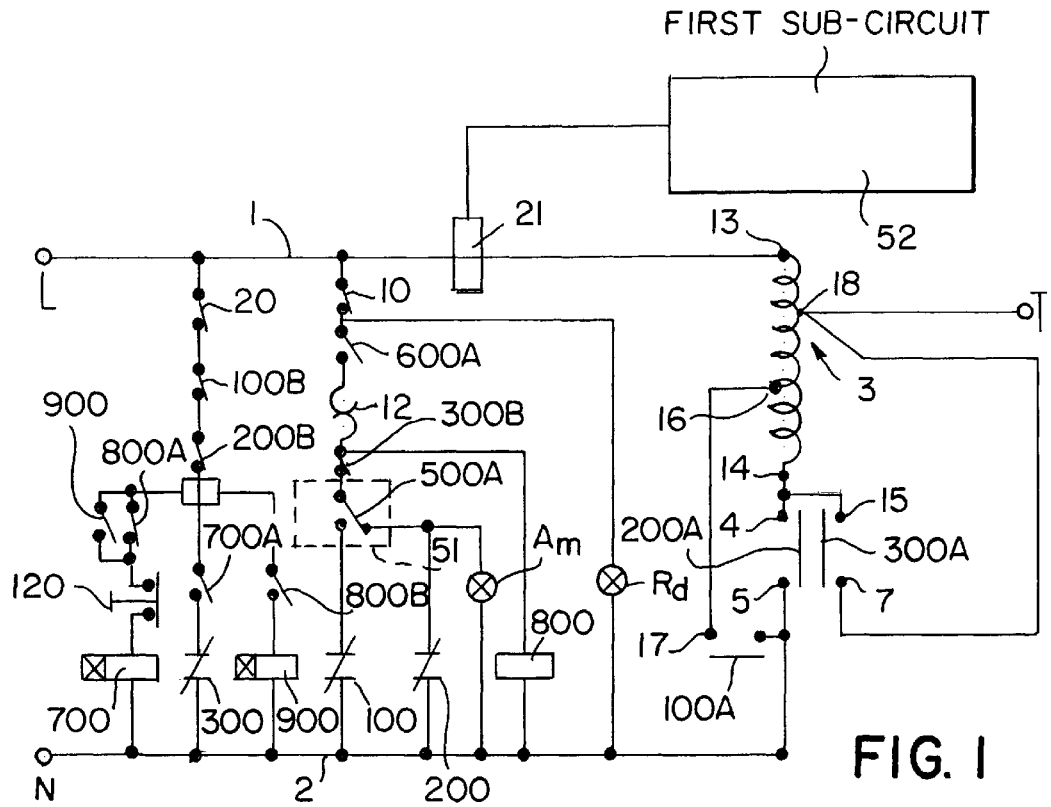
FIG. 1 illustrates a first electrical power control system embodying the present invention at start up.

Referring to FIG. 1, a positive rail 1 has a positive terminal L for connection to a source of electrical power (not shown) and a neutral rail 2 has a neutral terminal N for connection to the source of electrical power. A transformer winding 3 has a positive end 13 connected to the positive rail 1 and a neutral end 14 connected both to a terminal connection 4 and a terminal 15. The terminal connection 4 can be electrically connected to a terminal 5, which is connected to the rail 2, by device of a relay contact 200A and the terminal 15 can be electrically connected to a terminal 7 by device of a relay contact 300A. At a point 16 within the transformer winding, a terminal 17 is connected. The terminal 17 can be electrically connected to the terminal 5 by device of a relay contact 100A. The relay contacts 100A, 200A, and 300A are all normally open contacts. This is shown in FIG. 1. Only when their respective coils 100, 200 and 300 (described hereinafter) are energized, are the electrical connections made.

The transformer winding 3 is tapped at a predetermined point 18 which is connected to an output terminal T. In the present embodiment, the transformer winding 3 has 126 turns between point 16 and the neutral end 14, 126 turns between the point 16 and tapping point 18, and 14 turns between the tapping point 18 and the positive end 13. It will be apparent therefore that by suitable operation of the relay contacts 100A and 200A, either the connection of the neutral end 14 to the neutral rail 2 via terminal 5 or the connection of the point 16 to the neutral rail 2 via terminal 17 and terminal 5 can take place so that one of two selected reduced voltages can appear at terminal T.

The relay contact 300A is operated to short circuit the turns of the winding between point 18 and the neutral end 14 so that these are not able to be in an open circuit condition which would be detrimental to the condition of the transformer winding 3.

A sub-circuit of a monitoring device control circuit is connected between the rails 1 and 2. This sub-circuit comprises a fuse 10 having one end connected to the rail 1 and the other end connected to a terminal point of a normally open relay contact 600A. The relay contact 600A can make an electrical connection to a terminal point which is connected to one side of a heat sensor 12. The other side of the heat sensor 12 is connected both to a coil 800 and to a terminal point of a normally closed relay contact 300B. The relay contact 300B can make an electrical connection to a terminal point which is connected to a terminal point of a relay 500A contained with a box generally identified by reference numeral 51. The relay contact 500A can make an electrical connection either to a terminal point connected to the coil 100, which is connected to the rail 2, or to both a lamp Am (Amber), which is connected to the rail 2, and a terminal point connected to the coil 200, which is connected to the rail 2. A red lamp Rd is also connected from a point between fuse 10 and relay contact 600A, and the rail 2.

Another sub-circuit of the monitoring device control circuit is also connected between the rails 1 and 2. This sub-circuit comprises a fuse 20 having one end connected to the rail 1 and the other end connected to a terminal point of a normally closed relay contact 100B. The relay contact 100B can make an electrical connection to a terminal point which is connected to a terminal point of another relay contact 200B. The relay contact 200B can make electrical contact with a terminal point which is connected to a fault condition unit.

The fault condition unit comprises a DC power supply which provides a 12 volt supply to one terminal of a normally open relay contact 800B. The relay contact 800B can make an electrical connection to a coil 900 which is connected to the rail 2. Another 12 volt supply is connected to one terminal of a normally open relay contact 700A. The relay contact 700A can make electrical connection to the coil 300 which is connected to the rail 2. A further 12 volt supply is connected to a terminal of a normally closed relay contact 800A and a terminal of a normally open relay contact 900A. The relay contacts 800A and 900A can make electrical connection to one terminal of a manual reset switch 120. The other terminal of the manual reset switch 120 is connected to a coil 700 which is connected to the rail 2.

A current sensor 21 in the form of a toroid is wound around the rail 1. The output of the sensor 21 is connected to a first sub-circuit generally identified by reference number 52 and shown in detail in FIG. 4. As can be seen, the output of sensor 21 is connected to a conversion network 24. The network converts the current signal from sensor 21 and provides an output comprising a voltage which is proportional to the current flowing along the rail 1. The voltage output from the network 24 is connected to a step sensor 22 and a level sensor 23.

The step sensor 22 detects the rise in level of the input value from the network 24 against the preceding input value. In this way, it is possible to detect when the load connected to terminal T varies so that an increased voltage may be required, for example in the case of fluorescent lighting, the variation in load implies switching on of lighting.

To avoid incorrect sensing due to transients on the line due to switching of inductive components, a null circuit can be included which effectively stops the sensing for a brief period of time during switching of, say, relay contact 500A.

Each time the step sensor 22 detects an increase in current, a signal is sent to short timer 25 which is reset and started. The output of short timer 25 is sent to gate logic 26 for controlling a switch 27 to enable or disable the coil 500.

The level sensor 23 detects an initial current level and outputs a signal to a gate 28 for controlling a switch 29 to enable or disable the coil 600. In the event that the current level exceeds a predetermined maximum, the level sensor 23 outputs a signal to the gate logic 26.

A voltage sensor 30 detects the voltage on the positive rail 1 via a wipe located on the relay contact 600A. When the voltage drops below a certain level, a signal is sent to gate logic 26 and also to a long timer 31 which is reset and started. The output of the long timer is sent to the gate logic 26.

The electrical power control system described with reference to FIG. 1 operates as follows. FIG. 1 illustrates the initial position when power is first supplied to terminals L and N. In the initial 4 to 8 ms, an initial current flow occurs along rail 1 and through some turns of the winding 3 of the transformer to the output terminal T since the relay contacts 100A, 200A and 300A are in their normally open position, but those turns do not offer any significant impedance for such a short amount of time. In addition lamp Rd is lit via fuse 10 showing not only the presence of a supply voltage, but that fuse 10 has not blown. The current sensor 21 senses this flow of current. As a result, the level sensor 23 outputs a signal to gate 28 along line 40. The logic of gate 28 provides a signal to switch 29 so that coil 600 is supplied with current so as to energized the coil and hence close relay contact 600A.

As a result, a circuit is formed through fuse 10 and the now closed relay contact 600A. Current can therefore flow through the heat sensor 12, which detects a cool condition of the winding 3 at start up, through the normally closed relay contact 300B, and through relay contact 500A which is electrically connected to coil 200. Current also flows through the heat sensor to the coil 800. In addition, the lamp Am is lit.

Since coil 200 is now carrying current, the relay contact 200A closes to electrically connect the terminals 4 and 5 together so that the neutral end 14 of the winding 3 of the transformer is connected to the rail 2. Accordingly, current flows through all the turns of the winding 3. Thus, a voltage appears at terminal T which comprises 252/266 of the voltage at terminal L. The supply of this voltage is indicated by the lighting of lamp Am.

Figure 2:
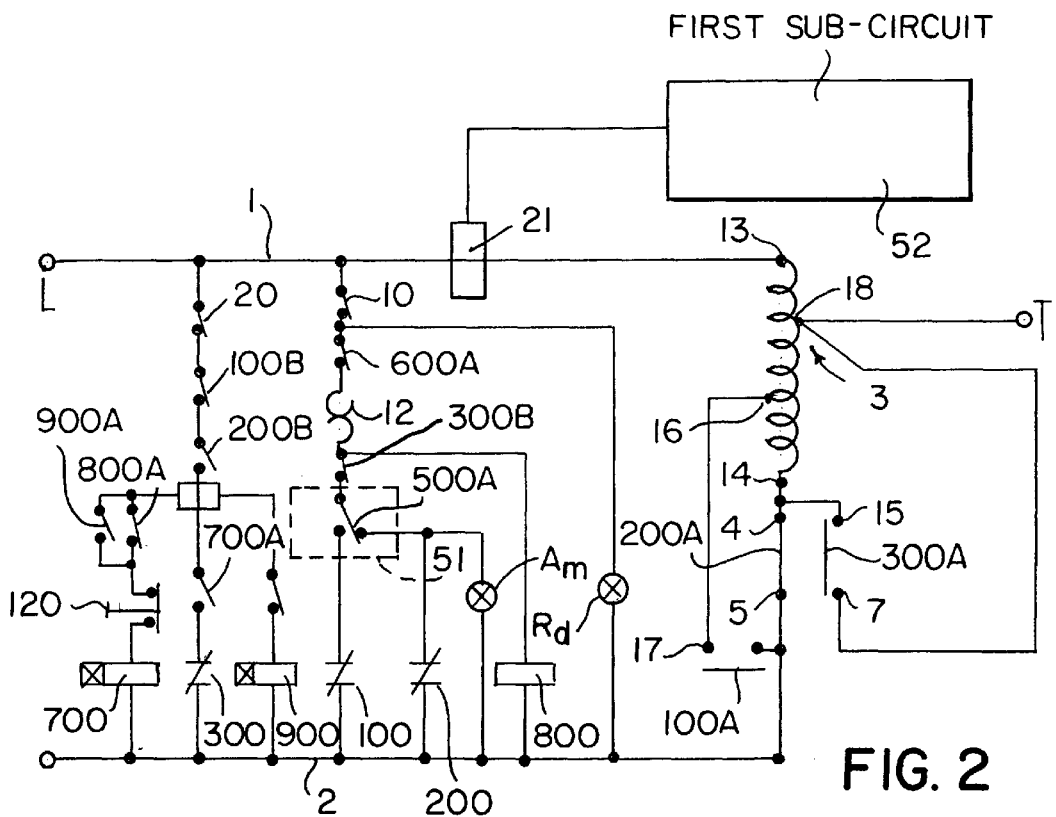
FIG. 2 illustrates the system of FIG. 1 after start up.

Since coil 800 is now carrying current, the relay contact 800B closes and the relay contact 800A opens. However, current will not flow for long through fuse 20 because with the energization of the coil 200, the relay contact 200B opens. It will be appreciated that coils 700 and 900 are designed to be slow to operate in response to energization (say 100 ms) so that the reaction of their respective relays does not take place before the relay contact 200B opens. Thus, there is no risk that coil 300 may become energized to close relay contact 300A. The above situation is shown in FIG. 2.

As noted above, the current sensor 21 senses the initial flow of current through rail 1. As a result, the step sensor 22 detects a step in the current and outputs a signal to short timer 25 and a signal to gate logic 26 along line 41. By device of the gate logic 26, the presence of a signal on line 41 inhibits switch 27 from energizing coil 500, which remains in its initial position. However, once the step sensor has detected the initial flow of current for a predetermined time, no further step is detected and hence the signal on line 41 disappears.

At the same time as the current sensor 21 senses the initial current, the voltage sensor 30 senses a voltage above a predetermined minimum level and outputs a signal to the long timer 31 and to the gate logic 26 along line 42.

Once the short timer 25 has timed out, a signal is output to the gate logic 26 along line 43. However, switch 27 does not energize coil 500 until the long timer 31 also times out and outputs a signal along line 44. In this way, there is no undue energization of coil 500 during periods of voltage instability. Nevertheless, once the voltage has become stable and remains so, the short timer 25 controls energization of coil 500.

In summary, the gate logic 26 will not operate to turn on switch 27 if there is a signal on line 41 indicating a step in current demand or if there is no signal on line 42 which indicates insufficient voltage or if both the short timer 25 and long timer 31 have timed out and output signals on their respective lines 43 and 44.

Figure 3:
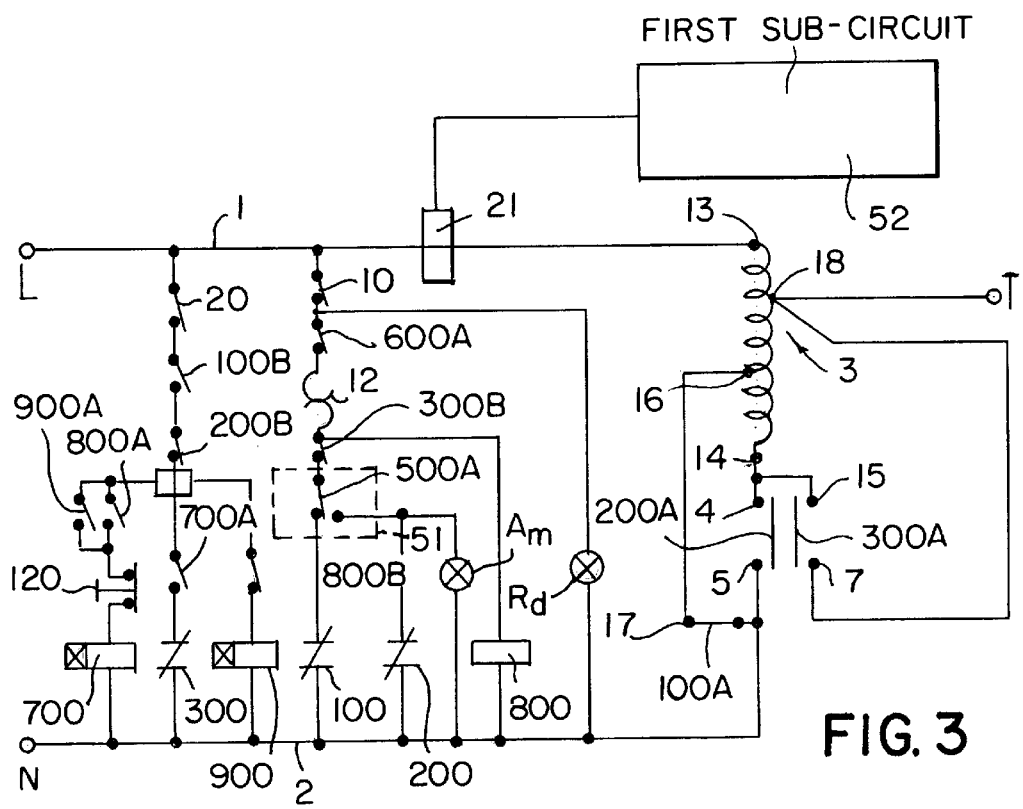
FIG. 3 illustrates the system of FIG. 1 after switching to output reduced voltage.

When the gate logic criteria have been met, then switch on of switch 27 occurs so that current flows through coil 500. As a result, relay contact 500A is moved to electrically connect to the relay terminal which is connected to the coil 100. Thus, current no longer passes through coil 200 which becomes de-energized whilst coil 100 now becomes energized. As a result, relay contact 101A closes and relay contact 200A opens. Thus, the turns of the winding 3 between the point 16 and 14 are eliminated. Consequently, a voltage appears at terminal T which comprises 126/140 of the voltage at terminal L. It will be appreciated that it is preferred that the relay contact 100A closes before the relay contact 200A opens. This situation is shown in FIG. 3.

In addition to the above relay contact movements, it will be understood that while relay contact 200B now closes and relay contact 100A opens, there remains no current flow through the circuit incorporating these relay contacts.

The circuit of this embodiment incorporates fault monitoring so as to provide a number of safety features.

In particular, the present embodiment can provide a failsafe condition in the event of failure of the relay contact operating coils, general overloading of the system, a fault external to the system creating an overload condition, a fault in the winding causing a thermal build up and operating the heat sensor 12, a fault causing the fuse 10 to blow, a disconnection in the sub circuit wiring causing the relay contacts 100A or 200A to release, and any failure which causes the winding to go open circuit.

The appearance of the failsafe condition is described below with reference to a number of examples. As long as current is flowing through rail 1 below a predetermined level, coil 600 remains energized and the relay contact 600A is closed. However, when the level sensor 23 detects a current above a maximum permissible current, a signal is output to gate 28 along line 45 and the logic of gate 28 makes switch 29 turn off so that coil 600 is no longer energized. As a result, relay contact 600A opens which de-energized coils 100, 200 and 800. As a consequence, the relay contacts 100A and 200A open and the relay contacts 100B, 200B and 800A close.

The latter three relay contacts closing provides for a flow of current which energizes coil 700 via manual reset switch 20. Thus, after about 100 ms, the coil 700 causes the relay contact 700A to close which provides a flow of current through coil 300. As a result, the relay contact 300A closes to connect terminals 15 and 7 thereby putting a short circuit across the primary turns of the winding 3 between points 18 and 14. Consequently, the magnetic field is collapsed so that the winding 3 ceases to operate as a transformer and offers substantially no impedance between points 13 and 18.

Since the full input voltage now appears at terminal T, closing relay contact 300A has the effect that the electrical power supply system of the present invention is bypassed. In addition, damage to the winding 3 that could otherwise occur from being open circuit is avoided so that a failsafe condition can be provided. In this respect, the situation of leaving such an open circuit should be considered. If an open circuit occurs for any length of time, there will be a voltage drop between points 13 and 16, in the present case 24 volts, so that the electrical power supply system of the present invention is not bypassed and hence a true failsafe condition is not provided. Furthermore, there will be a reversing energization of the winding which will lead to an unpleasant and disturbing vibration in the form of a hum or buzz. In addition, the winding will eventually reach a saturation voltage across the open circuit part of the winding. This saturation voltage can reach quite high values, in the present case of the order of 760 volts, which is not only potentially very dangerous to anyone who should accidentally touch the system but can also produce sparking due to breakdown of the insulation thereby producing a winding insulation failure.

Figure 4:
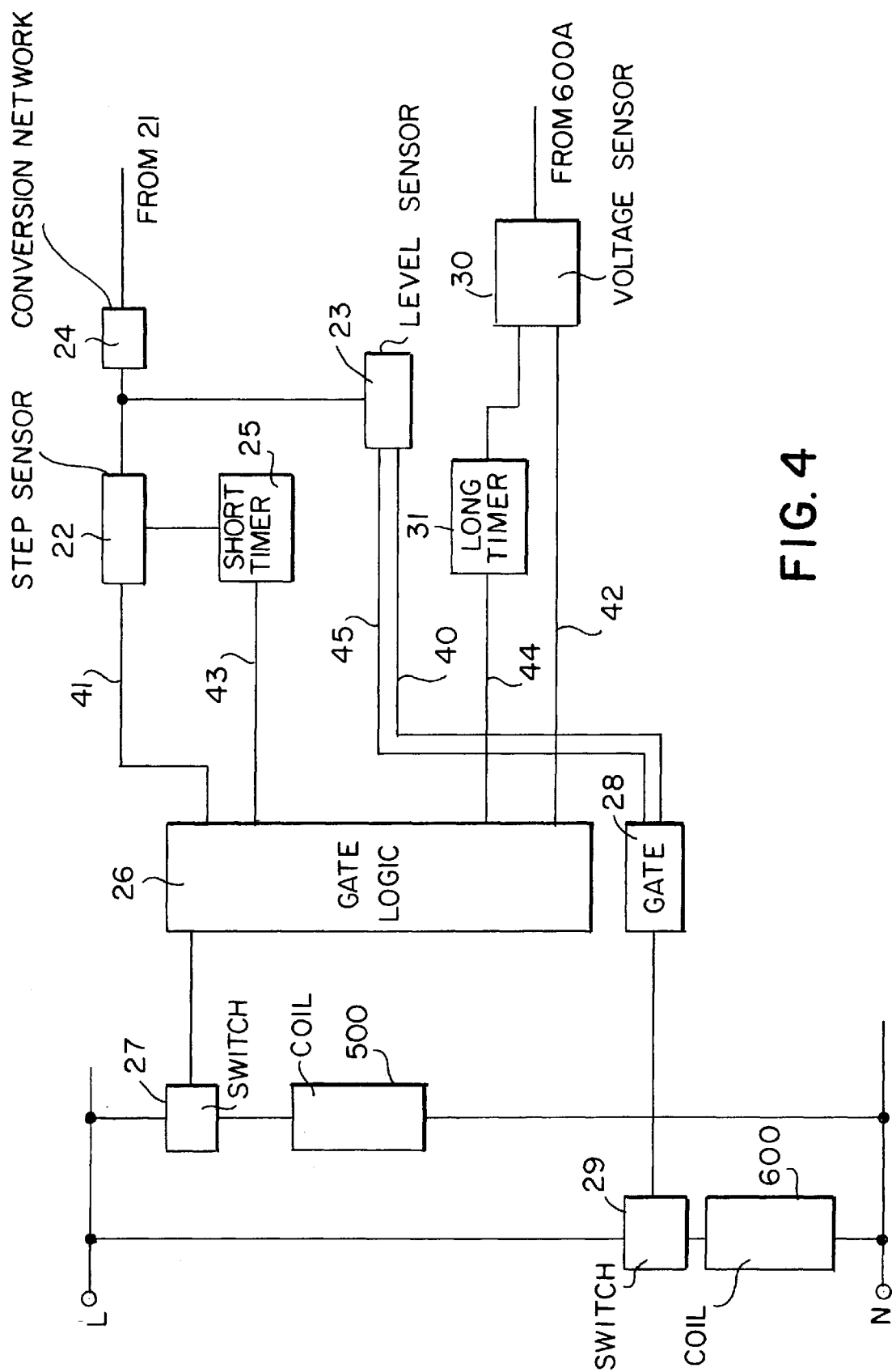
FIG. 4 illustrates a sub-circuit involved in controlling operation of the system shown in FIG. 1.

It should be noted that the energization of coil 300 opens relay contact 300B so that electrical operation of coils 100 and 200 and their respective relay contacts is inhibited. If the current flowing along rail 1 drops again, the signal along line 45 disappears and gate 28 turns switch 29 back on so that coil 600 is again energized. This leads to a closing of relay contact 600A with the effect that relay contact 300A opens and either relay contact 100A or 200A closes depending upon the output from logic gate 26. Preferably, the sub-circuit shown in FIG. 4 is arranged such that the relay contact 200A closes when current flows again along rail 1. This can be achieved by making sure that long timer 31 is reset, say by interrupting the voltage sensing of voltage sensor 30. In this respect, it will be noted that regardless of the current flows if the voltage on rail 1 drops below the predetermined level, long timer 31 is reset so that relay contact 500A automatically returns to the position connected to coil 200.

When the electrical power supply system of the present invention is in use, if the heat sensor 12 breaks due to overheating, current no longer flows to coils 100, 200 and 800 with the result that relay contacts 100A, 200A and 800 open. Thus, relay contact 300A is closed with the same effects as above.

When the heat sensor 12 again detects an appropriate temperature and closes, current can again flows to coil 800. As a result, relay contact 800A opens breaking the current path to coil 700. This results in its relay contact 700A opening so that current no longer flows to coil 300. The effect of this is for its relay contact 300B to close to again provide current to energize coil 100 or 200. It will be appreciated that although relay contact 800B is closed, coil 900 is slow to operate so that relay contact 900A does not operate in time to provide an alternative current path to coil 700. Thus, the system is restarted.

Another fault monitoring concerns the situation if either relay contacts 100A or 200A should open due to mechanical or electrical failure. Although contact 800B is closed due to current flowing through coil 800, coil 900 is not provided with current because either relay contact 100A or 200B is open. However, with the mechanical or electrical failure, that open relay contact will close so that current is now supplied to coil 900. After about 100 ms, relay contact 900A will close so that current is supplied to coil 700 via manual switch 20 which eventually causes relay contact 300A to operate as above. It should be noted that this locks the system so that physical inspection of the system is required. However, power will still be supplied to the load connected to terminal T.

In a similar manner, should relay contact 800A or coil 800 fail, a similar failsafe condition can still be attained.

It will be appreciated that operation of relay contact 300A while relay contacts 100A or 200A are actuated is prevented not only electrically, but also mechanically by interlocking the contacts so that relay contact 300A is positioned between the relay contact 100A and 200A so that operation of either of them inhibits operation of relay contact 300A and operation of relay contact 300A inhibits relay contact 100A and 200A.

It will also be appreciated that once the failsafe condition has been attained, the system can be returned to normal running by actuation of the reset switch 20 which breaks the current supply to coil 700 which will then break the supply of current to coil 300 so that relay contact 300A opens and either relay contact 100A or 200A closes.

Figure 5:
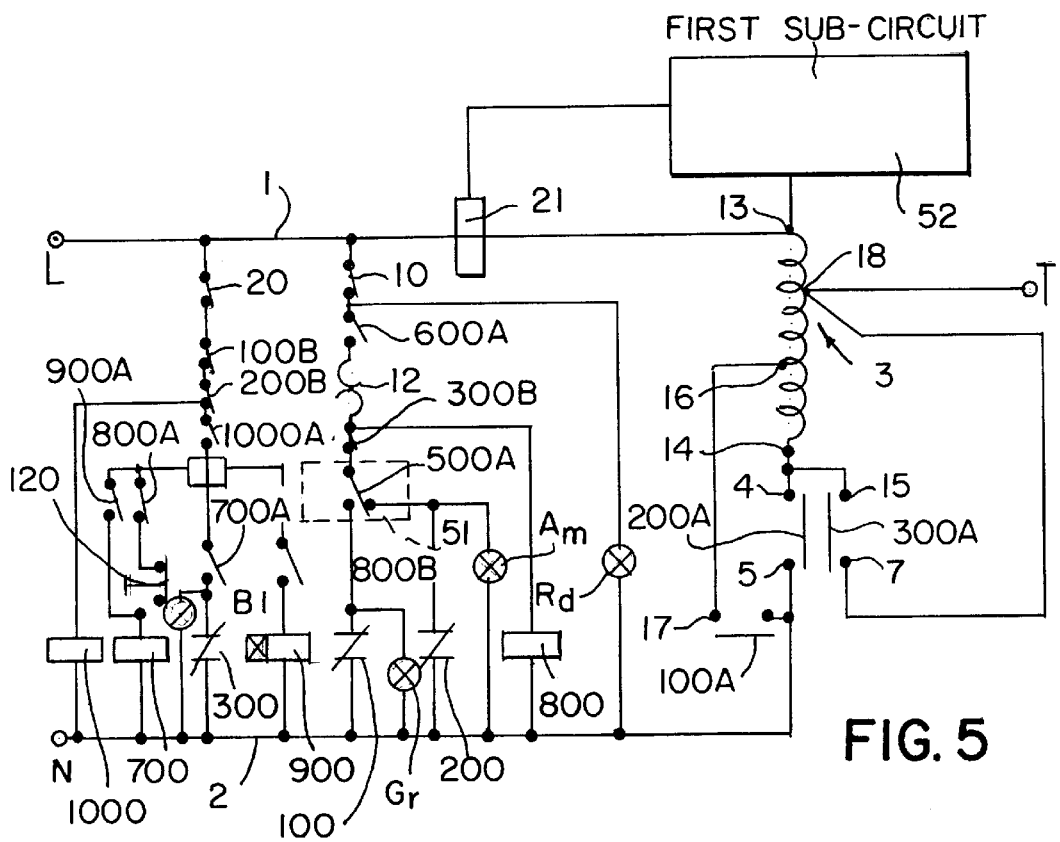
FIG. 5 illustrates a second electrical power control system embodying the present invention at start up.

FIG. 5 illustrates a second embodiment of the present invention wherein common components with the first embodiment bear common reference numerals.

Referring to FIG. 5 it can be seen that the sub-circuit containing fuse 20 has been modified. In particular, the fault condition unit has been changed. The relay contact 200B is now connected to one terminal of a normally open relay contact 1000A and to a coil 1000 which is connected to the rail 2. The relay contact 1000A can make electrical connection to one terminal of the relay contact 800B, to one terminal of the normally open relay contact 700A, to one terminal of the normally closed relay contact 800A, and to one terminal of the normally open relay contact 900A. The remaining connections are common to FIG. 1.

In addition to the above, a green lamp Gr is connected across the coil 100 and a blue lamp Bl is connected across the coil 300. Thus, when lamp Rd is lit, a user knows that the system is connected into circuit and that a voltage exists on rails 1 and 2 and that fuse 10 has not blown, when lamp Am is lit that a voltage resulting from relay contact 200A is being provided at the output terminal T, when lamp Gr is lit that a voltage resulting from relay contact 100A is being provided at the output terminal T, and when lamp Bl is lit that a fault condition has occurred.

It will be apparent that at initial start up of the embodiment in FIG. 5, current flows through relay contacts 100B and 200B through to coil 1000. However, coil 1000 is slow to operate so that relay contacts 100B or 200B open before relay contact 1000A can close. Thus, the various functions of the fault condition unit do not have current supplied to them.

In the circumstances of a fault condition, the effect is to close both the relay contacts 100B or 200B so that current is supplied to coil 1000. After the built in time delay, relay contact 1000A closes to supply current to the fault condition unit so that it can operate as described above.

It will be understood that the embodiment illustrated shows an application of the invention in one form only for the purposes of illustration. In practice, the invention may be applied to different configurations, the detailed embodiments being straightforward for those skilled in the art to apply.

For example, while the embodiments described are connected to operate so that relay contact 200A disconnects as relay contact 100A connects, relay contact 200A can be left connected while relay contact 100A connects.

In addition, while two relay contacts 100A and 200A are provided to enable the supply of two selected voltages at terminal T, further relay contacts can be provided to enable the supply of more than two selected voltages.

While the embodiments are described for use with a mains supply of 240 volts at 50 cycles, other mains voltages and frequencies can be used, for example, 110 volts or 277 volts at 60 cycles.

The embodiments described are fully automated with automatic reset and constant sensing for faults. However, while the present embodiment describes th& switching from the relay contact 100A to the relay contact 200A in the circumstances of when power demand occurs when switching a load connected to terminal T, when a low incoming voltage occurs, when any failure in the sub circuit of FIG. 4 occurs or when any circuit fault creating current fluctuation in excess of a predetermined level, costs can be saved by incorporating fewer responses to these circumstances. For example, in simpler forms of the invention, some of these aspects can be omitted to save costs, say the short and long timer can be replaced by a simple time delay relay to switch relay contact 500A. Similarly, the voltage sensor and step sensors shown in FIG. 4 can be omitted.

In addition, the relay contact 500A in box 51 is shown as a relay contact which can be operated by a coil. It will be appreciated that control of the operation of the relay contact within box 51 can take many forms. For example, it can be dependent on a complex of timers, for example as shown in FIG. 4, or it can be dependent on a time delay relay. The latter is particularly appropriate for the control of loads having just one or two units, such as street lighting.

Although mechanically operated relay contacts could be employed, it will be apparent that electronically operated switches could be used as an alternative. However, it should be noted that by having the relay contacts 100A and 200A located as the neutral end of the winding 3, much smaller switching currents are encountered than with prior art arrangements. Indeed, by use of the present invention, it has been possible to dramatically reduce the power rating of the relay contacts required. For example, a 20 KVA system can be handled with the relay contact rating of a 2 KVA system without the deterioration normally associated with switching large inductive loads. Thus, extremely high reliability is assured.

While the current sensor 21 is located on the rail 1, it will be appreciated that the current sensor could be located on the rail connected to terminal T.

Thus, the present embodiment provides a system which can output a voltage which can be switched between a level approximating to mains voltage (or a chosen voltage) and a fully reduced level at switch on of the load, and to a reduced voltage value which does not produce a noticeable drop in effect on the load, say illumination of lighting, but which provides a substantial improvement in economy while all the time providing a secure and reliable failsafe condition in the event of a fault thereby enhancing the safety of the system and ensuring that the system complies with various legal requirements.

It will be apparent that although the present invention has been described in connection with an fluorescent lighting, it will be apparent that the present invention can be applied to other lighting systems and other loads in general.

I claim:

1. A method of controlling an electrical power system for providing one of a plurality of selected voltages to a load, the method comprising the steps of:

(a) electrically connecting one end of a winding to the positive terminal of a source of electrical power, the winding being tapped at a predetermined position for supplying an output terminal with a selected voltage;

(b) enabling a terminal connection device to electrically connect the other end of said winding to a neutral terminal of said source of electrical power in response to supply of power being required;

(c) excluding a predetermined number of turns of said winding in response to a request for another selected voltage;

(d) monitoring for at least one type of fault condition; and (e) electrically disconnecting the winding from the neutral terminal and electrically short-circuiting said other end of the winding to said predetermined position when a fault condition is detected.

2. A method according to claim 1 wherein step (c) comprises disabling the terminal connection means to electrically disconnect the other end of said winding from the neutral terminal and enabling a switching means to electrically connect to the neutral terminal to exclude the DV predetermined number of turns of said winding from said other end of the winding.

3. A method according to claim 2 wherein step (c) comprises disabling said terminal connection means and said switching means and enabling a further switching means to electrically short-circuit said other end of said winding to the predetermined position.

4. A method according to claim 1 further comprising the step of monitoring for an increased load demand and stopping step (c) in response to a predetermined load demand.

5. A method according to claim 1 further comprising the step of monitoring the voltage to said one end of the winding and stopping step (c) in response to the voltage falling below a predetermined value.

6. A method according to claim 1 further comprising the step of supplying the request for another selected voltage after the lapse of a predetermined time interval following supply of power being required.

7. An electrical power control system for providing one of a plurality of selected voltages to a load, the electrical power control system comprising:

a positive and neutral terminal for connection to a source of electrical power;

an output terminal for supplying a plurality of selected voltages;

a winding having one end electrically connected to the positive terminal and being tapped at a predetermined position for supplying the output terminal with a selected voltage;

a terminal connection means for electrically connecting the other end of the winding to the neutral terminal;

a switching means for excluding a predetermined number of turns of said winding in response to a request for another selected voltage;

monitoring means for monitoring at least one type of fault condition; and further switching means for electrically short-circuiting said other end of the winding to the predetermined position when a fault condition is detected.

8. A system according to claim 7 wherein said switching means is connected to the neutral terminal to exclude the predetermined number of turns of said winding from said other end of the winding.

9. A system according to claim 8 wherein in response to monitoring of a fault condition, said monitoring device disables the terminal connection means and said switching means to electrically disconnect said other end of the winding from the neutral terminal and enables the further switching means.

10. A system according to claim 7 wherein said monitoring means further comprises a current demand sensing device for sensing for transient current changes in the current demand by the load; wherein said monitoring means disables the switching means in response to transient changes in current above a predetermined level.

11. A system according to claim 7 wherein said monitoring means further comprises a current overload monitoring means for monitoring current to the winding; wherein said monitoring means disables said terminal connection means and said switching means to electrically disconnect said other end of said winding from the neutral terminal and enables said further switching means in response to a monitored current above a predetermined maximum level.

12. A system according to claim 7 wherein said monitoring means further comprises a voltage monitoring means for monitoring voltage to said one end of the winding; and wherein said monitoring means disables said switching means in response to a voltage below a predetermined minimum.

13. A system according to claim 7 wherein said monitoring means further comprises timer means for measuring said time starting from a supply of said selected voltage; wherein said monitoring means enables said switching means when said measured time exceeds a predetermined time interval.

14. A system according to claim 13 wherein said timer means monitors a further time starting from supply of said selected voltage; wherein said monitoring means enables said switching means only when said further time exceeds a further predetermined time interval during which said voltage to said one end of said winding has not fallen below a predetermined minimum.

15. A system according to claim 13 wherein said timer means is reset whenever said switching means is disabled or said further switching means is enabled.

16. A system according to claim 7 wherein the terminal connection means, the switching means and the further switching means comprise relay contacts.

17. A system according to claim 16 further comprising a zero crossing detector so that movement of the relay contacts can take place at optimum points during said cycle.

* * * * *